United States Patent [19]

Hurwitz et al.

[11] 4,351,158
[45] Sep. 28, 1982

[54] METHOD OF PRODUCING MULTICOMPONENT LYOPHILIZED PRODUCT

[75] Inventors: Arthur Hurwitz; John Michelucci, both of Plattsburgh, N.Y.; John Krupey, Montreal, Canada

[73] Assignee: American Home Products Corporation, New York, N.Y.

[21] Appl. No.: 114,151

[22] Filed: Jan. 22, 1980

[51] Int. Cl.³ .............................................. B65B 63/08
[52] U.S. Cl. .............................................. 62/60; 34/5; 62/66; 62/74; 141/9; 141/11; 141/100
[58] Field of Search ...................... 34/5; 62/1, 60, 65, 62/66, 74; 141/9, 11, 69, 82, 99, 100, 129; 222/129, 132

[56] References Cited

U.S. PATENT DOCUMENTS

| | | | |
|---|---|---|---|
| 2,803,888 | 8/1957 | Cerletti | 34/62 X |
| 3,129,673 | 4/1964 | Stanley et al. | 141/100 X |
| 3,269,905 | 8/1966 | Damaskus et al. | 206/459 |
| 3,579,360 | 5/1971 | Rey | 34/5 X |
| 3,616,543 | 11/1971 | Barclay | 34/5 |
| 3,862,302 | 1/1975 | Price et al. | 424/12 |
| 3,932,943 | 1/1976 | Briggs et al. | 34/5 |
| 4,001,944 | 1/1977 | Williams | 34/5 |
| 4,060,911 | 12/1977 | Weiler et al. | 34/5 |
| 4,162,003 | 7/1979 | Bartos et al. | 34/5 X |

Primary Examiner—Frederick R. Schmidt
Attorney, Agent, or Firm—Adley F. Mandel

[57] ABSTRACT

At least two incompatible solutions are simultaneously charged into a container maintained at a temperature substantially below the freezing temperature of each solution in such predetermined amounts that the separate charges of solution freeze on the walls and are then lyophilized.

9 Claims, 7 Drawing Figures

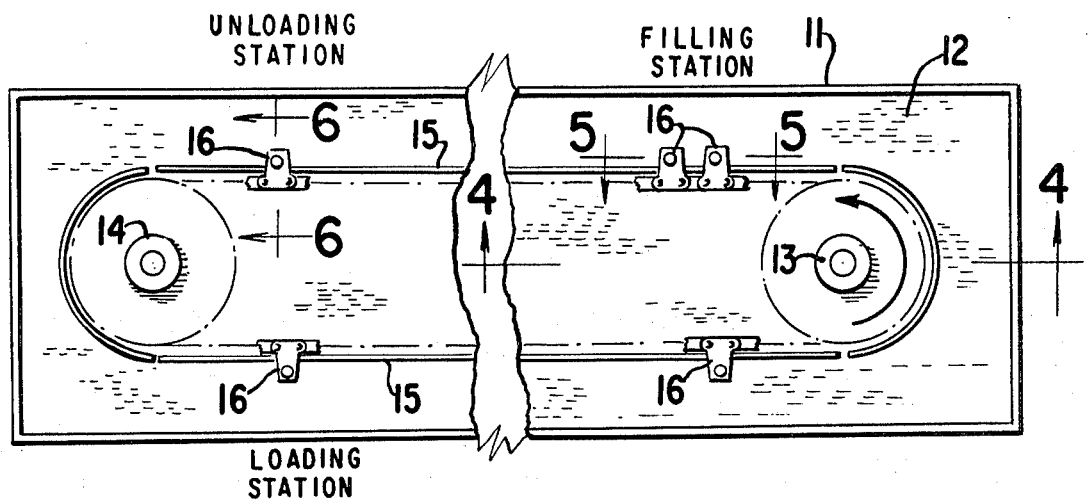
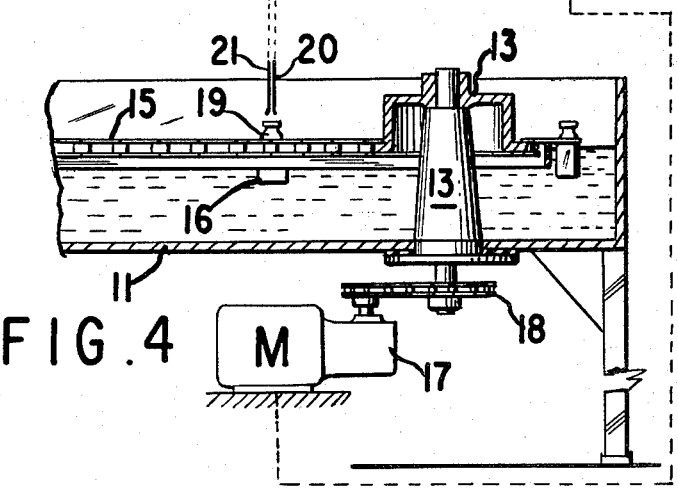
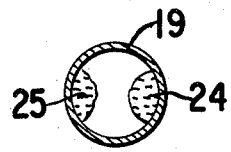
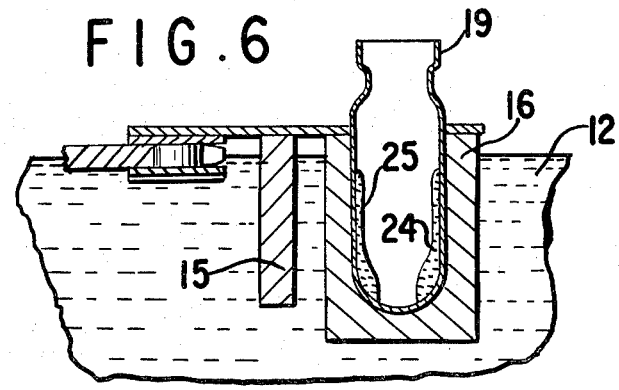
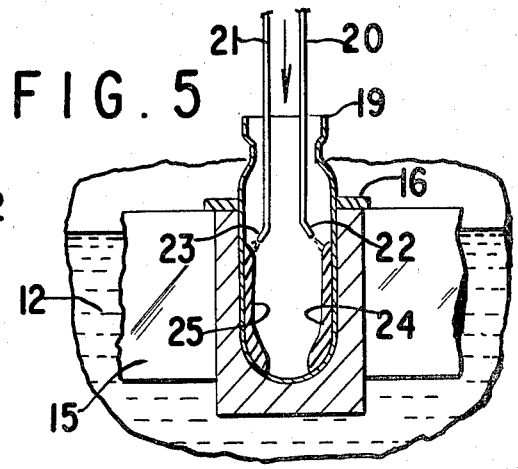

METHOD OF PRODUCING MULTICOMPONENT LYOPHILIZED PRODUCT

BACKGROUND OF THE INVENTION (a) Field of the Invention

This invention relates to a process for obtaining a package containing at least one mass of dry matter comprising at least two materials incompatible with each other in the presence of moisture.

(b) Description of the Prior Art

Various methods have been employed in the past to obtain a package containing at least two materials incompatible with each other in the presence of moisture.

In U.S. Pat. No. 3,269,905, a method is described in which reagents which may be incompatible with each other in the presence of moisture are subjected to freezing in successive layers in a container and thereafter freeze-drying the frozen strata.

In U.S. Pat. No. 3,616,543, a method is described in which reagents which may be incompatible with each other in the presence of moisture are sequentially charged in liquid form into a container with freezing of the charge and rotation of the container between charges so that the separate charges do not touch, and then lyophilizingthe frozen charges.

In U.S. Pat. No. 3,862,302, a method is described in which reagents in solution are separately formed into frozen and freeze-dried beads or spheres and then placed into a container for lyophilization.

SUMMARY OF THE INVENTION

According to this invention at least two materials which may be incompatible in the presence of moisture are simultaneously charged as liquid compositions into a container maintained at a temperature substantially below the freezing temperature of each of the incompatible compositions. The liquid compositions are charged in such predetermined amounts that the separate charges freeze on the walls. The frozen masses are then lyophilized. Preferrably the container is an upright container.

In one embodiment of the invention, the liquid compositions are charged directly into the bottom of an upright container. In a second embodiment which provides a more cautionary approach, the liquid compositions are charged onto the opposite side walls of the container. This latter approach is preferred when the quantities of the liquid compositions are such that they do not instantaneously freeze upon contact with the cooled container. When the charged quantities are such that they do not instantaneously freeze and the materials are especially incompatible (very reactive) then the liquid compositions are charged onto the upper portions of the opposite side walls of the container.

In a especially preferred embodiment the separate liquid compositions are precooled to a temperature slightly above their freezing point and then simultaneously charged into the container. The use of precooled liquid composition is especially useful wherein the upright container comprises a receptacle with a small surface area or one which is shallow. An example of such a receptacle is found in a Microtiter ® plate manufactured by Cooke Laboratory Products of Alexandria, Virginia. This plate contains a multiplicity (96) of shallow "vee" shaped wells or "u" shaped cupules.

DESCRIPTION OF THE INVENTION

The process of the invention will now be described in connection with the accompanying drawings wherein the liquid compositions are charged onto the opposite side walls of an upright container and in which:

FIG. 1 is a front view of a reagent vial showing two lyophilized reagents adhering to each side;

FIG. 2 is a cross-sectional view taken along line 2—2 of FIG. 1.

FIG. 3 is a top view of a system for loading, filling and unloading reagent vials;

FIG. 4 is a side elevation of the filling system taken along line 4—4 of FIG. 3.

FIG. 5 is an enlarged view of a reagent vial being filled in the system of FIG. 4 taken along line 5—5 of FIG. 3.

FIG. 6 is an enlarged view of a filled reagent vial in the system of FIG. 4 taken along line 6—6 of FIG. 3.

Figure 7:
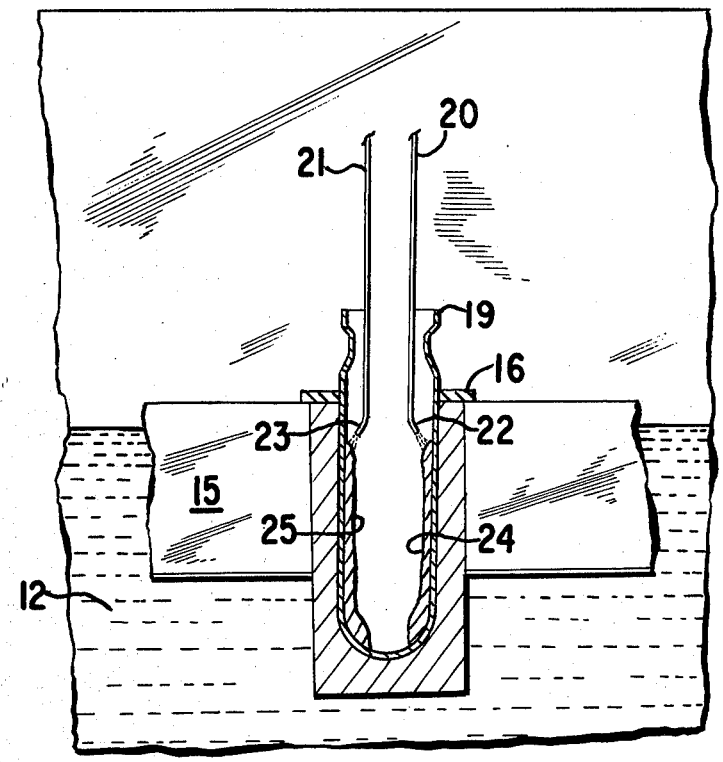
FIG. 7, is an enlarged view of another embodiment of a reagent vial being filled.

In one aspect of the process of the invention, FIG. 3 shows a receptacle 11 containing a body of freezing liquid 12 such as liquid nitrogen. Mounted within receptacle 1 are sprockets 13 and 14 which support revolving chain 15 having attached thereto reagent bottle holders 16. Referring now to FIG. 4, sprocket 13 is driven by motor 17 through belt drive assembly 18. Motor 17 is controlled through a control circuit and synchronized with a filling machine to align empty reagent bottles 19 for filling. Depending from the filling machine are pipettes 20 and 21 shown in raised position in FIG. 4 and in lowered position inside reagent bottle 19 in FIG. 5. Pipettes 20 and 21 have tips 22 and 23 respectfully, directed outwardly towards the side-walls of reagent bottle 19. Each reagent solution or suspension is pumped through a proportioning pump in the filling machine, thereby measuring a predetermined amount of solution per unit time, into pipettes 20 and 21 each of which discharges a predetermined, accurately measured amount of reagent onto the sides of reagent bottle 19, which reagents 22 and 23 immediately freeze to the side of the bottle and do not mix at the bottom, as is shown in FIG. 6. Reagent bottles 19 are removed from holders 16 at the unloading station and placed in racks for lyophilization after which they are capped with cap 26 and ready for use as shown in FIG. 1.

The process of the invention will be illustrated with respect to reagents for an immunological or diagnostic test for detecting the presence of human chorionic gonadotrophin (hCG) in urine, which test is utilized in the diagnosis of pregnancy. The particular reagents employed are those described in co-pending application U.S. Ser. No. 806,563, filed June 14, 1977, now abandoned in favor of a continuation in part application, and U.S. Pat. No. 4,123,343, granted Oct. 31, 1978, both said patent and application being herein incorporated by reference in their entirety.

However, it will be appreciated by those skilled in the art that the process of the invention is equally applicable to a wide range of analytical, immunological, and diagnostic reagents which employ at least two essentially incompatible materials in a single container.

EXAMPLE I

Pregnancy Test Reagents

Immunologic and antiserum compositions useful as reagents in hemagglutination inhibition tests for pregnancy were prepared. Stabilized hCG sensitized red blood cells were suspended in a lyophilization medium which contained a suitable carbohydrate diluent, buffer, sodium chloride, normal rabbit serum, merthiolate and EDTA. Antiserum (to hCG) at a level adjusted to give a predetermined test sensitivity was prepared separately in the same lyophilization medium. Simultaneously, 50 microliters of each, the cell suspension and the antiserum solution, were injected onto the inner surface of a siliconized round bottom vial having an internal diameter of 12–16 mm which was precooled in an acetone-dry ice bath at about −70° C. and were instantaneously frozen. The frozen reagents were lyophilized immediately in a freeze dryer for 16–20 hours at about 75 to 200 micron Hg. The dried materials performed as anticipated when tested for specified sensitivity to hCG.

EXAMPLE II

Pregnancy Test Reagents

Sensitized red blood cell suspension and antiserum solution were prepared as described in the art and Example I and having quantities adjusted so that volumes of 50 microliters or less contain the material necessary to give a predetermined test sensitivity. Simultaneously, the reagents were injected into the bottom of a precooled siliconized round bottom vial and were instantaneously frozen. The frozen reagents were lyophilized in a freezer dryer for 16–20 hours at about 75 to 200 microns Hg. The dried materials performed as anticipated when tested for specified sensitivity to hCG.

EXAMPLE III

Pregnancy Test Reagents

Sensitized red blood cell suspension and antiserum solution were prepared as described in the art and Example I and having quantities adjusted so that volumes of 50 microliters or less contained the material necessary to give a predetermined test sensitivity. The two reagent solutions were cooled to a temperature of 2°–4° C. and then simultaneously injected from an automatic pipette into the bottom of a series of wells contained in a Microtiter ® plate which had been precooled in a dry ice-isopropanol mixture and were instantaneously frozen. The plate containing the reagents was lyophilized in a freeze dryer for 16–20 hours at about 75 to 200 microns Hg. The plate in the freeze dryer rested on a dry ice, pre-cooled aluminnum block. The dried materials performed as anticipated when tested for specified sensitivity to hCG.

We claim:

1. A process for obtaining a package containing a mass of dry matter comprising at least two immunologic reagent materials incompatible with each other in the presence of moisture which comprises the steps of simultaneously charging separate aqueous liquid compositions of each material into a container maintained at a temperature substantially below the freezing temperature of each of said first and second liquid compositions in such predetermined amounts that the separate charges of liquid compositions freeze on the wall of said container, and then simultaneously lyophilizing the frozen masses.

2. The process of claim 1 wherein the charge of one liquid composition consists essentially of a predetermined immunologically effective amount of a suspension of sheep erythrocytes sensitized with human chorionic gonadotropin.

3. The process of claim 2 wherein the charge of a second liquid composition consists essentially of a predetermined immunologically effective amount of human chorionic gonadotropin antiserum together with phosphate buffer.

4. The process of claim 1 wherein said container is an upright container.

5. The process of claim 4 wherein the simultaneous charging of the liquid compositions is directed to the bottom of the upright container.

6. The process of claim 4 wherein the simultaneous charging of the liquid compositions is directed onto the opposite side walls of the upright container.

7. The process of claim 4 wherein the simultaneous charging of the liquid compositions is directed to the upper portions of opposite side walls of the upright container.

8. The process of claim 1 wherein the separate liquid composition are precooled to a temperature slightly above their freezing point prior to charging said compositions into the container.

9. The process of claim 8 wherein said container comprises a shallow receptacle.

* * * * *